United States Patent
Garvey, III et al.

[11] Patent Number: 5,219,353
[45] Date of Patent: Jun. 15, 1993

[54] SURGICAL ENDOCLIP

[76] Inventors: Thomas Q. Garvey, III, 10125 Gary Rd., Potomac, Md. 20854; Kathleen Ruddy, 50 Green Village Rd., Madison, N.J. 07940; Frank V. Gates, 9 Yale Dr., Succasunna, N.J. 07876

[21] Appl. No.: 843,755

[22] Filed: Feb. 28, 1992

[51] Int. Cl.$^5$ .............................................. A61B 17/00
[52] U.S. Cl. .................................. 606/157; 606/158; 24/563; 24/564
[58] Field of Search ............... 606/103, 120, 157–158; 24/457, 543, 563, 703.6, 704.1, 564

[56] References Cited

U.S. PATENT DOCUMENTS

| | | | |
|---|---|---|---|
| 2,568,511 | 9/1951 | Ogden | 24/253 |
| 2,598,901 | 6/1952 | Garland | 606/120 |
| 2,626,608 | 1/1953 | Garland | 606/120 |
| 3,463,156 | 8/1969 | McDermott | 606/158 |
| 3,705,586 | 12/1972 | Sarracino | 24/543 |
| 5,062,846 | 11/1991 | Oh et al. | 606/158 |

Primary Examiner—Stephen C. Pellegrino
Assistant Examiner—Gary Jackson
Attorney, Agent, or Firm—Levisohn, Lerner & Berger

[57] ABSTRACT

A surgical endoclip intended to be used with conventional instruments for applying surgical clips, such as those marketed by the United States Surgical Corporation (U.S. Surgical), is disclosed in which the clip fits within and is operated by the movable jaws in the U.S. Surgical Applier but the clip is constructed so as to provide a circumferential closing of the clip around the duct or vessel. The conventional movement of the jaws of the applier operates with the initially open surgical clip, which under pressure by the parallel movement of the jaws, closes about the duct or vessel being occluded.

7 Claims, 7 Drawing Sheets

SURGICAL ENDOCLIP

BACKGROUND OF THE INVENTION

This invention relates to a new and improved surgical endoclip adapted to be used with either the well known U.S. Surgical Corporation type applier which has achieved widespread use and sometimes is known by the trademark Auto Suture or a modification thereof.

Surgical endoclips are metal devices used to occlude ducts or vessels during surgical procedures. When two clips are applied to a duct or vessel the duct can be severed between them, and if the clips are properly applied and secured, leakage of fluid, such as blood or bile is prevented. Ultimately, the structure occluded by the clip is permanently stenosed and sealed by normal healing processes. The device used to apply an endoclip can be used for both open and closed, laparoscopic, surgical procedures.

Prior endoclips, made of titanium, are generally U-shaped with the legs squeezed together to seal a vessel. Such clips have a tendency to come off the ducts or vessels to which they have been applied, in part, because the legs may tend to spread apart. Clips have been observed coming off along the transverse axis along which they had been applied as they were being placed and immediately after they had been placed. Such clips also can work themselves off in the severed end of the duct or vessel along the long axis. In either case, the vessel lumen would cease to be effectively occluded, and bile or blood would be free to leak into in postoperative patients which has sometimes led to surgical reexploration, transfusion therapy and other untoward complications. Since these problems are not uncommon, the inventors have provided a new endoclip to reduce the risk of slippage after application.

One of the approved current clips is designed so that the inner surfaces of the U-shaped arms are smooth. Another current clip is designed so that the inner surfaces of its U-shaped arms are corrugated. However, after application, both clips are open and free at one end, even though they are squeezed down across the duct and thus, may slip off the duct along its transverse axis. The occlusions created by and the positions of these clips across the duct are maintained solely by virtue of titanium's lack of "memory"—i.e., once crimped, the clips tend to remain crimped. These clips are not secured in any way other than by squeezing or crimping them across the duct after the clip has been properly placed.

U.S. Surgical Corporation has been very successful in promoting its Auto Suture Disposable Clip Applier. This applier is the subject of several U.S. patents, for instance, U.S. Pat. Nos. 4,242,902 and 4,616,650. These patents illustrate that the surgical clips are fed in a cartridge-like fashion between two jaws 103 (FIGS. 14-19 of U.S. Pat. No. 4,616,650), and the patents illustrate the operation of the U.S. Surgical Clip applier and the cartridge fashion in which such clips are supplied.

U.S. Pat. No. 4,834,096 disclosed a plastic ligating clip which uses a special manual instrument to close the plastic clip and stop the flow of fluid. The subject of the '096 patent is directed to a plastic clip which, in part, is to eliminate metal clips which are objectionable for the reasons set forth in the '096 patent. The '096 clip closes completely around the vessel to which it is secured. The '096 patent presents a special instrument to apply the plastic clip, and the plastic clip is unable to be used with the U.S. Surgical Auto Suture.

There are several other clip tool manufacturers that supply tools that apply clips "manually" i.e., one at a time, "muzzle loaded". This invention is adapted to be used with such surgical clip appliers.

An object of this invention is to provide a surgical clip which may be used with widely accepted types of surgical clip appliers, such that the clips are supplied in a cartridge form to be applied one after another by the surgical clip applier.

Another object of this invention is to provide such a surgical clip which circumferentially surrounds the duct to be closed in a more effective and efficient fashion than prior clips so as to prevent the slippage of such improved endoclips from the duct.

Still another object of this invention is to provide such an improved surgical clip which will find ready acceptance in the medical field, may be easily utilized with existing technology and provide enhanced benefits.

Another object of this invention is to provide such a surgical endoclip with nubbins formed on a holding surface thereof to further hold the clip on the duct being occluded when the clip is closed.

Yet another object of the present invention is to positively secure the ends of titanium surgical clips together to ensure the clip's attachment to a vessel.

Other objects, advantages and features of this invention become more apparent from the following description.

SUMMARY OF THE INVENTION

In accordance with the principles of this invention, the above objects are accomplished by providing a metallic endoclip, which is formed of a thin metallic unitary member generally of an elliptical cross section. The endoclip has a base which terminates at one end in an upwardly and rearwardly extending section which itself terminates in a lower free-end. The endoclip also has an upper forwardly extending arm terminating in an upper free-end which is spaced rearwardly from said lower free-end. The base and upper arm are connected by an upwardly extending section bent forwardly toward the free-ends of the endoclip. When parallel jaws exert inwardly directed parallel forces against the base and upper arm, the upper arm is displaced downwardly toward the base, and the upper free-end moves downwardly until it contacts the base. As the parallel jaw pressure continues to be exerted on the upper arm and base the upper free-end moves forwardly until it is captured by the bend formed by the rearwardly extending section and is trapped there as the upper arm and lower base move together to circumferentially surround the vessel. The positive lock formed by the rearwardly extending section bearing against the upper free-end ensures that the surgical clip can not open while in place on the vessel. As a further feature of this invention, a nubbin is provided upon the inner surface of the base in order to further ensure the attachment of the clip to the vessel, and the nubbin may also be shaped to puncture the vessel as the clip is applied to the vessel. As still a further feature of this invention, the free end of the upper arm cooperates with a grove formed in the upper surface of the base to fit therewithin and be prevented from lateral movement as the clip is closed.

DETAILED DESCRIPTION

Figure 1:
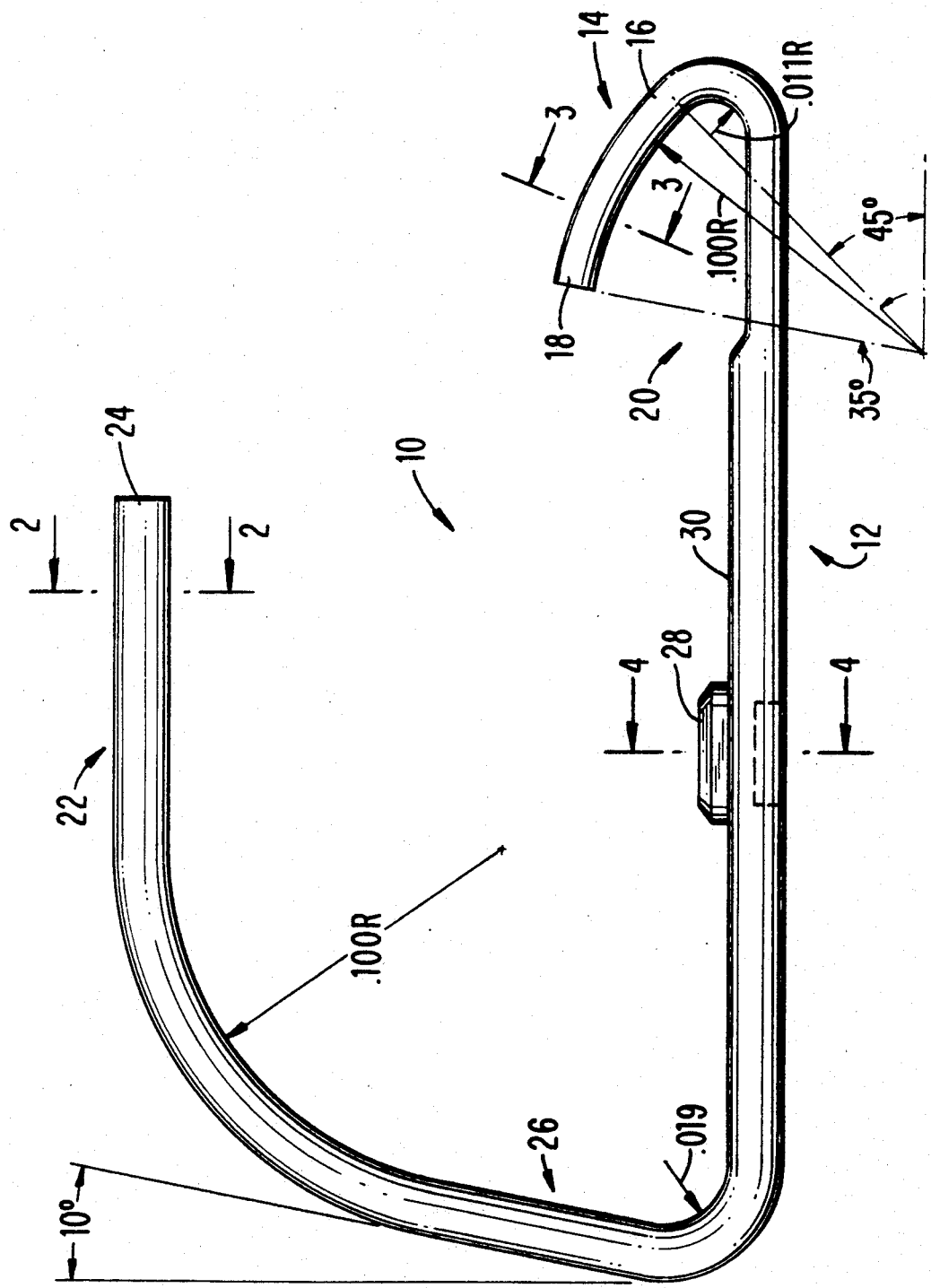
FIG. 1 is an end view of an embodiment of the surgical clip of this invention.

FIG. 1 is an end view of the endoclip of this invention, generally designated with numeral 10. The endoclip is formed of a thin metallic unitary member generally of an elliptical cross section. Because of its bio-compatability, Titanium is the preferred metal. The endoclip 10 has a lower straight base 12 which terminates at one end 14 in an upwardly and rearwardly extending section 16, which itself terminates in a lower free-end 18. A corner 20 is formed where section 16 turns rearwardly. The endoclip 10 has an upper forwardly extending arm 22 terminating in an upper free-end 24 which is spaced rearwardly from said lower free-end 18. The base 12 and upper arm 22 are connected by an upwardly and forwardly extending section 26. A nubbin 28 is formed on the inner surface 30 of base 12.

Figure 2:
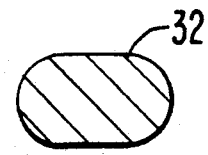
FIG. 2 is a sectional taken along lines 2—2 of FIG. 1.
Figure 3:
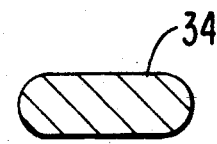
FIG. 3 is a sectional taken along lines 3—3 of FIG. 1.
Figure 5:
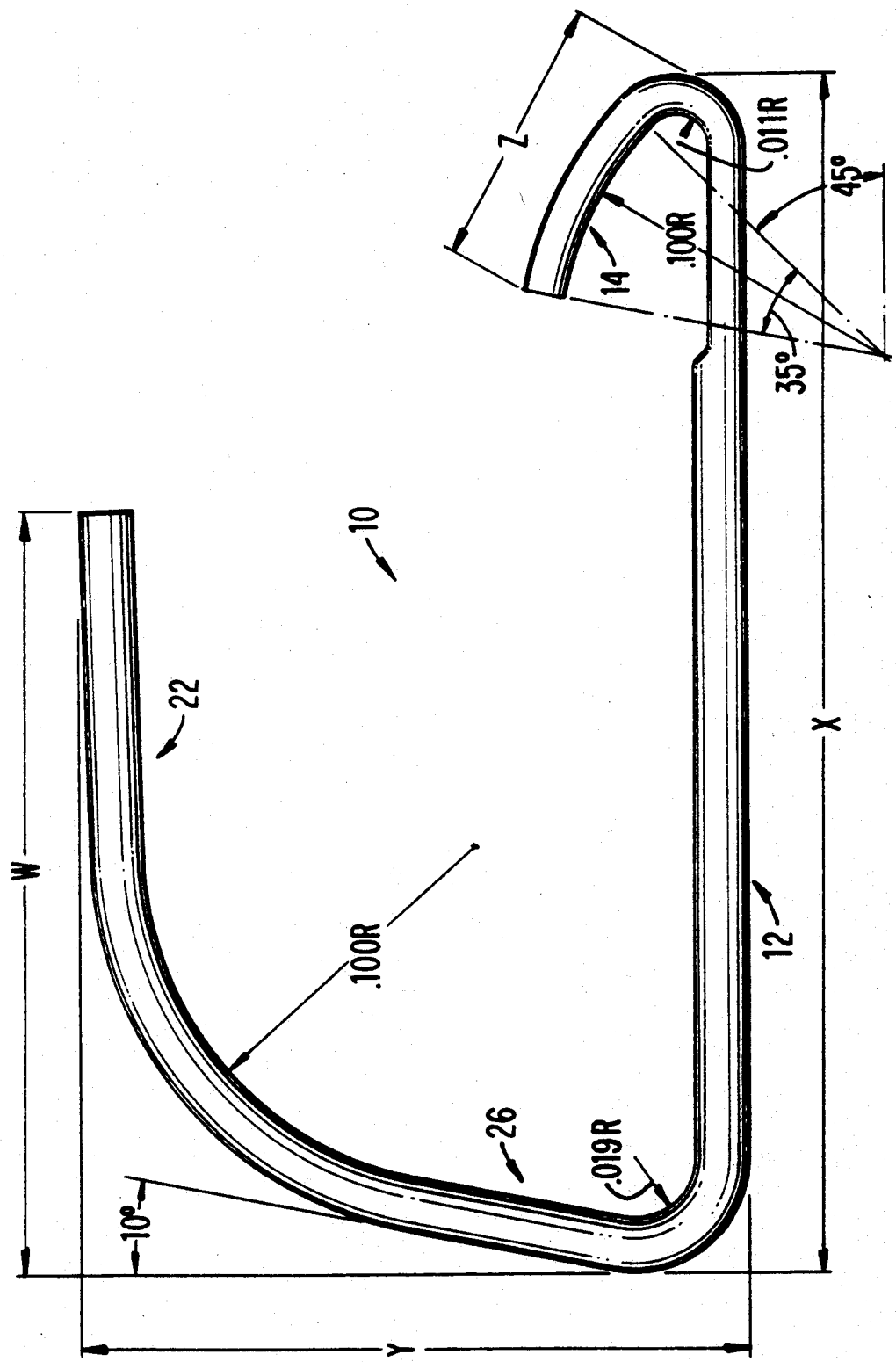
FIG. 5 is an alternate embodiment of the surgical clip of this invention without a nubbin with the clip shown in its open initial position.
Figure 6:
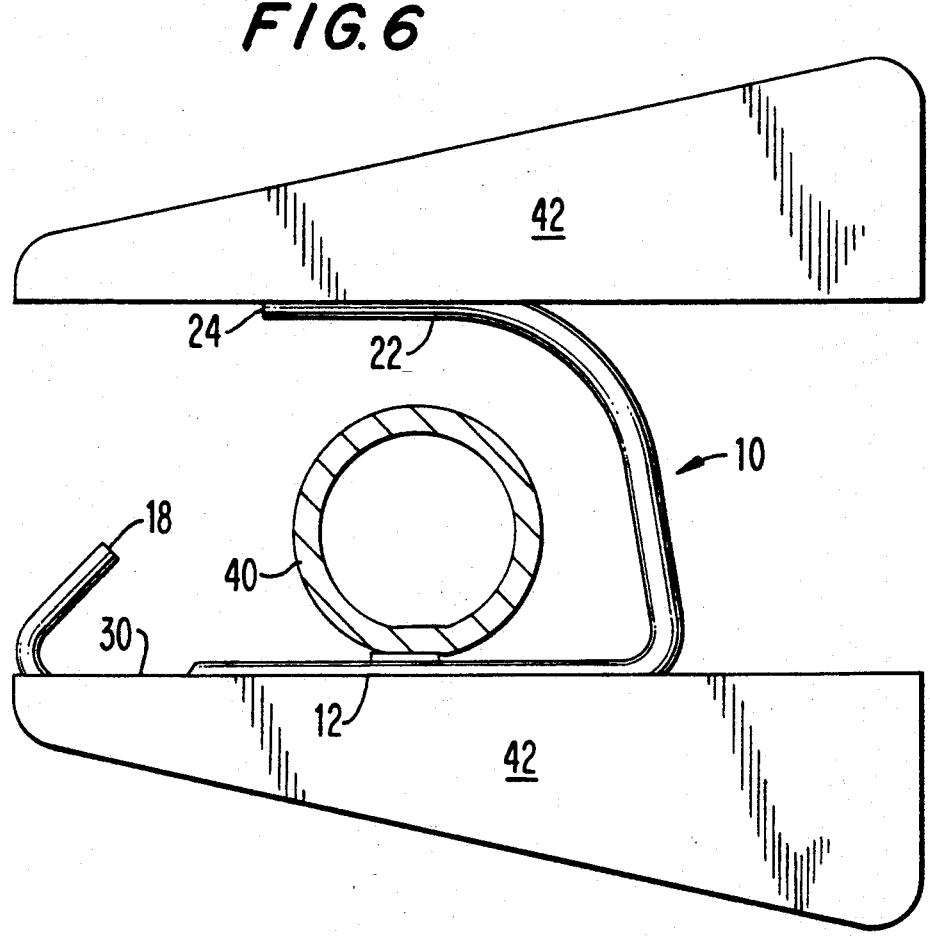
FIGS. 6-10 illustrate the surgical clip of this invention as it is closed and applied to the vessel.
Figure 7:
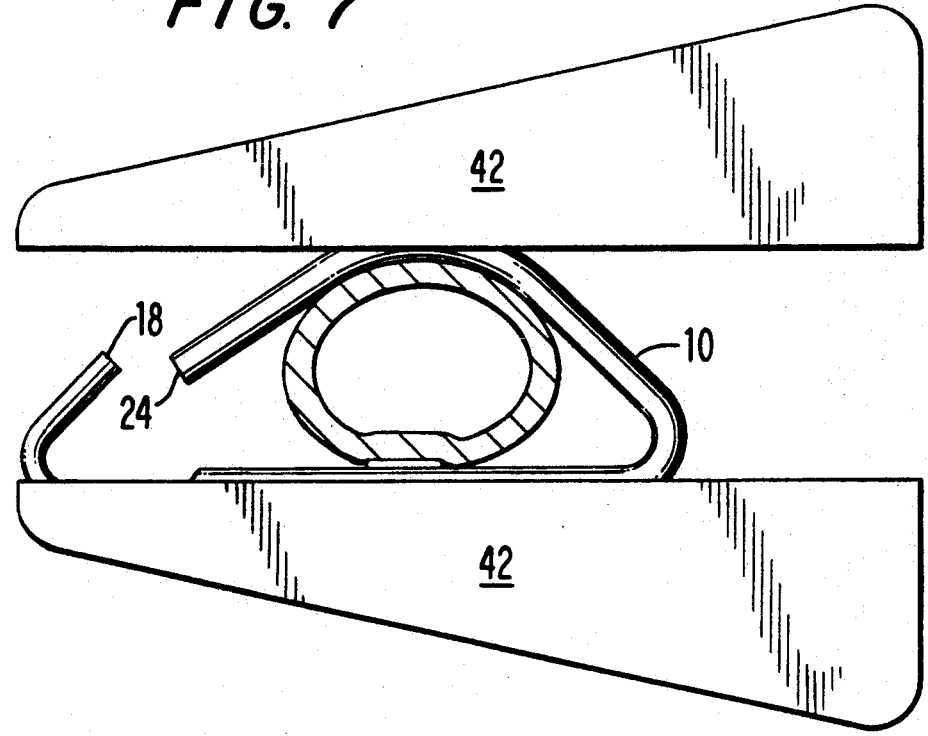
Figure 8:
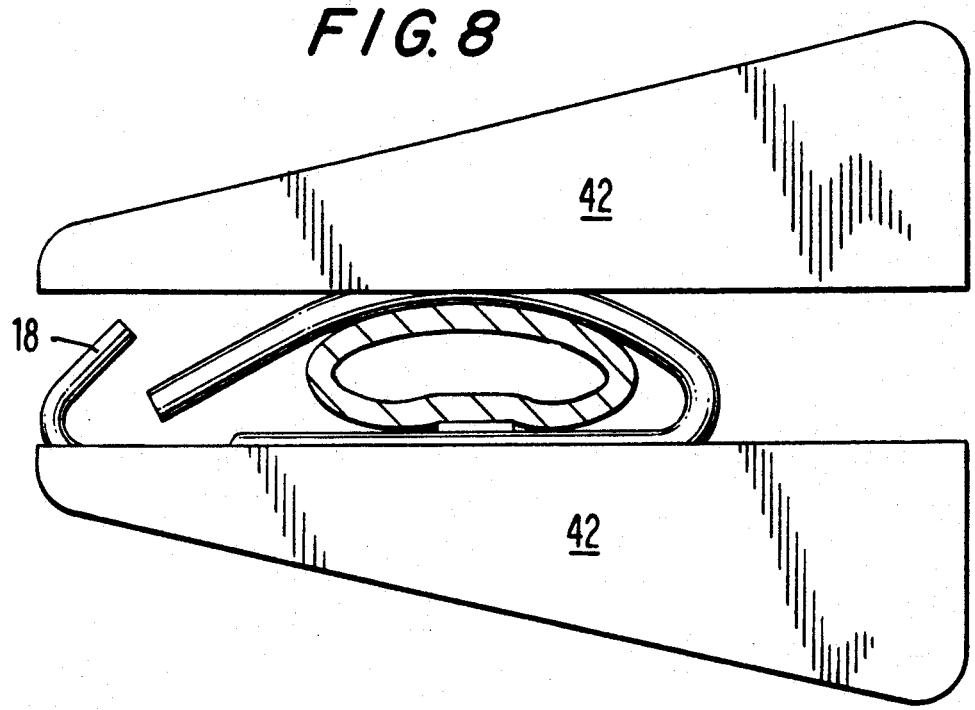
Figure 9:
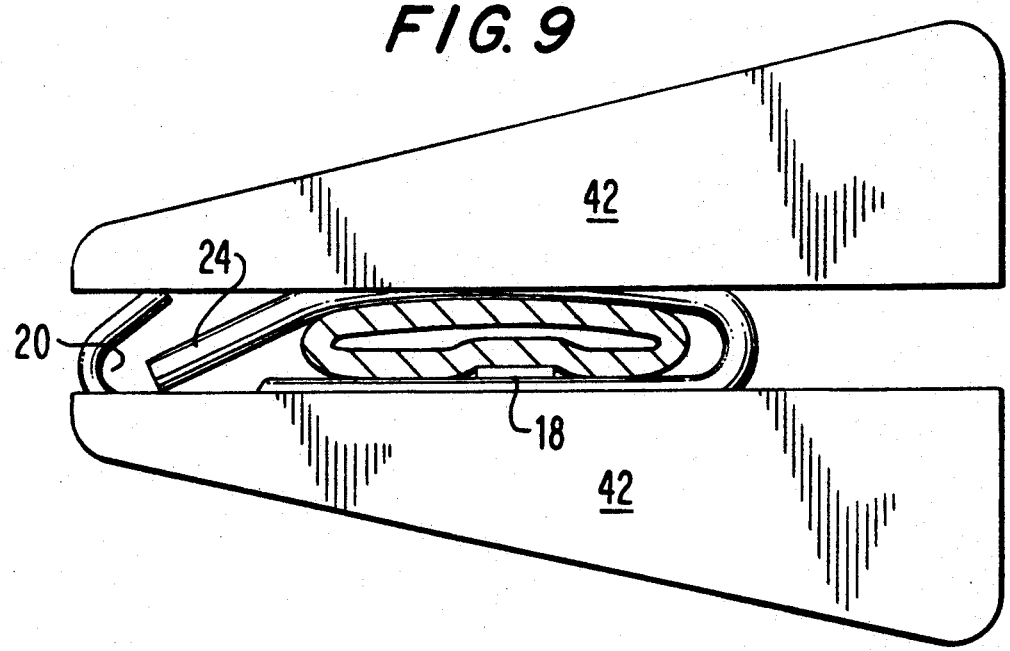

Specific angles and radii are shown in FIG. 1 for the endoclip. FIG. 5 shows the same endoclip having the same form, radii and angles as depicted in FIG. 1, but without the nubbin. Sectional views 2, 3 and 4 taken along lines 2—2, 3—3 and 4—4 illustrate the preferred shapes of the cross-sections of the specific section identified of the endoclip. In particular, the endoclip 10 has substantially uniform elliptical cross section 32 illustrated in FIG. 2—2 which is formed for most of the endoclip, with the forward end 34 of the base 12, the corner 20 and rearwardly extending section 16 having a smaller elliptical cross section as illustrated in FIG. 3. This enables the corner portion of the clip when fully closed to have a substantially uniform cross section, since the thickness of corner portion is smaller than the cross section for the remaining portion of the clip as illustrated in FIG. 2.

Figure 4:
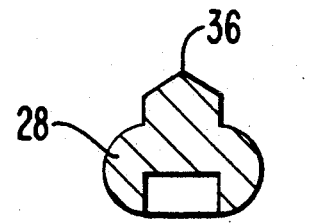
FIG. 4 is a sectional taken along lines 4—4 of FIG. 1.

As illustrated in FIG. 4, the nubbin 28 is provided with a pointed upper surface 36 adapted to pierce the vessel to which the endoclip is attached to further secure the endoclip to the vessel.

As described, this invention is intended to be used with a device similar to that of the Auto Suture sold by U.S. Surgical. As described in U.S. Pat. No. 4,616,650, jaws 103 move in parallel planes towards each other, and such Auto Suture or a modified version thereof is intended to be used with the endoclip of this invention.

FIG. 5 is a view of the Endoclip of this invention without nubbin 28. The same numerals apply for the same parts, and the radii and angles are the same as for FIG. 1.

Although the clip will work at any scale, the preferred embodiment of some important proportionalities as illustrated in FIG. 5 are:

$$\frac{Z}{X} = .222$$

$$\frac{Y}{X} = .614$$

$$\frac{W}{X} = .558$$

With these ratios, the clip is unlikely to effectively work if:

W increases by approximately 5% or decreases by approximately 10%

Figure 10:
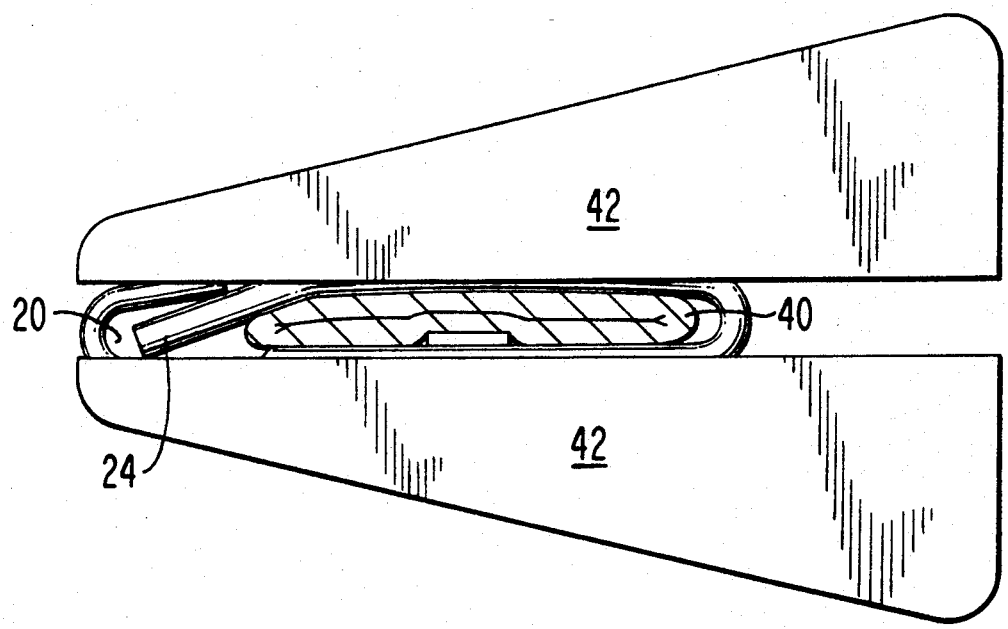

FIGS. 6-10 illustrate the endoclip in successive stages of deformation as it is applied to occlude a vessel 40. When the parallel jaws 41-42 exert inwardly directed forces against the base 12 and upper arm 22, the upper arm is displaced downwardly toward the base and the upper free-end 24 moves downwardly until it abuts the inner surface 30 of the base 12. As the jaw forces continue to be exerted on the upper arm 12 and base 10 the upper free-end 24 moves outwardly until it is captured by corner 20 and is trapped there. As the upper arm 22 and base 12 move further together to circumferentially surround the vessel, the upper free-end 24 is locked into the corner 20 and is positively held there by lower free-end 18. Further inward motion of the jaws causes contact between the upper jaw and free end 18. The free end then collapses, pinching the free end 24 between base 14 and free end 18. This positive lock ensures that the surgical clip circumferentially surrounds the vessel and will not open while in place on the vessel. Nubbin 18 further insures that the clip 10 will stay in place on the vessel. FIG. 10 illustrates the final shape of the deformed endoclip 10 gripping the duct or vessel 40.

The new endoclip 10 of this invention would initially be placed across the transverse axis of the duct 40, and it will be squeezed down in such a way that the clip 10 will end up surrounding and squeezing the duct while the ends of the clip are held together. The inward nubbin 18 on one or both arms of the clip 10 provide significant resistance to movement of the clip along the long axis of the duct.

Figure 11:
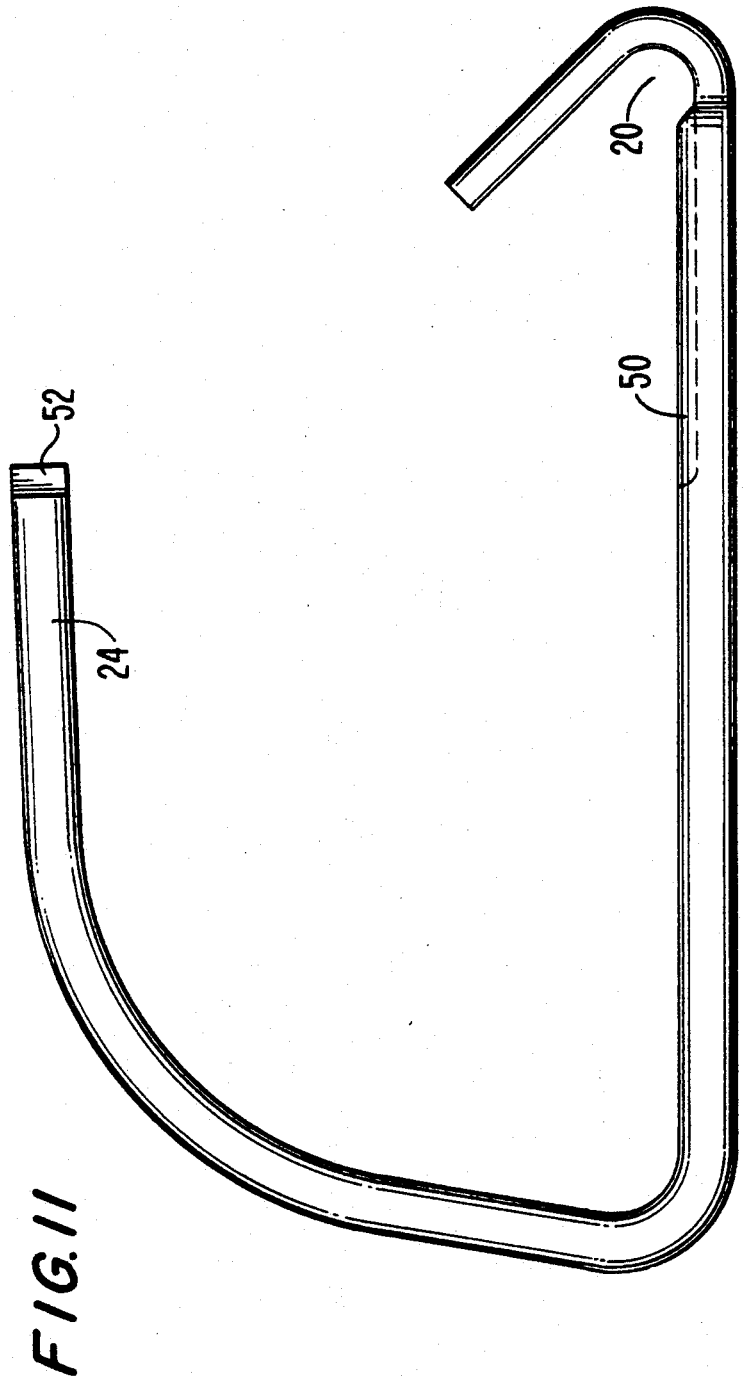
FIG. 11 is an end view of another embodiment of this invention with features that limit lateral movement of the mating clip motions.
Figure 12:
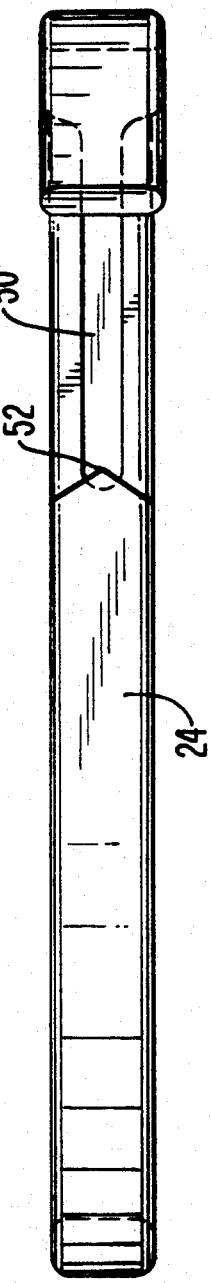
FIG. 12 is a top view of the embodiment of FIG. 11.

FIGS. 11 and 12 present yet another embodiment of this invention in which lateral movement between upper free end 24 and the base 12 is restrained by forming a groove 50 in upper portion 30 of the base and a Vee 52 on the upper free end 24 so that Vee 52 fits into groove 50 as the upper arm 22 moves downward and is captured in the corner 20. Lateral movement between the ends of the clip is thus restrained and the upper arm 22 is aligned with base 12 further ensuring the circumferential secure closing of the clip.

In summary, the new endoclip 10 would incorporate three novel elements:

1. One or two "nubbins" or a ridge, on the inner surface in contact with the vessel or ducts of one or both arms of the clip which, after application of the clip, would substantially increase resistance to slippage in both parallel and orthogonal directions with respect to the long axis of the occluded vessel or duct;

2. Complete, circumferential contact of the clip with the duct or vessel; and

3. Fixation of the ends of the clip together in such a way as to reduce greatly dependence on titanium's lack of "memory" or springiness for maintenance of the vessel or duct closure.

This invention has been described in its preferred embodiment, but modifications therefrom may be made by those of ordinary skill in the art which would still come within the scope and teachings of this invention as set forth in the appended claims.

We claim:

1. A surgical endoclip comprising a thin metallic unitary member comprising a base terminating in a forward end in an upwardly and rearwardly extending section, said upwardly and rearwardly extending section terminating in a lower free-end, a corner formed between said lower free-end and said forward end of said base, said endoclip further comprising an upwardly and forwardly extending intermediate section extending from the rearward end of said base, said upwardly and forwardly extending intermediate section terminating in an upper arm substantially parallel to said base, said upper are terminating in an upper free-end, said surgical endoclip having an open position with said surgical endoclip lying within an initial plane, said surgical endoclip deformable to a closed position by pressure applied to said upper arm and base to displace said upper free-end to be captured and clamped in said corner under said lower free-end to form a circumferential closure on a duct to be sealed with said endoclip, said upper free-end and the upper surface of said base having complementary contours along the direction of relative movement between said upper free-end and said base as said upper free-end moves to be captured in said corner, said upper free-end being moved into and along said complementary surface of said base as said endoclip is being closed and the upper free end is moving forwardly toward said corner, said complementary contours guiding the proper closure to maintain the ends within said initial plane as said endoclip is being closed and preventing the ends of said upper-free-end and said lower free-end from projecting out from the closed endoclip to prevent piercing of surrounding tissue.

2. A surgical endoclip as set forth in 1, wherein said metallic member comprises a bio-compatable metal.

3. A surgical endoclip as seth forth in 2, wherein said metal is titanium.

4. A surgical endoclip as set forth in 3, wherein said base member comprises means to hold said duct.

5. A surgical endoclip as set forth in 4, wherein said means to hold said duct comprises a nubbin.

6. A surgical endoclip as set forth in 5, wherein said nubbin comprises a sharp upper surface adapted to pierce and hold said duct.

7. A surgical endoclip as set forth in claim 1, wherein the forward surface of said upper free-end comprises a Vee shape and the complementary surface of said base comprises a groove to receive and hold said Vee as said endoclip is closed.

* * * * *

UNITED STATES PATENT AND TRADEMARK OFFICE
CERTIFICATE OF CORRECTION

PATENT NO. : 5,219,353
DATED : June 15, 1993
INVENTOR(S) : Thomas Q. Garvey, III; Kathleen Ruddy and Frank V. Gates It is certified that error appears in the above-indentified patent and that said Letters Patent is hereby corrected as shown below:

In the Title: Change "ENDOCLIP" to --CLIP--

In the Abstract: Line 1, change "endoclip" to --clip--

At each of the following occurrences, change "endoclip" to --clip--:

Column 1, in the heading
           line 6
           line 10
           line 17
           line 21
           line 36

Column 2, line 16
           line 23
           line 37
           line 39
           line 41
           line 46

Column 3, lines 20-21
           lines 23-24
           line 29
           line 35 (each occurrence)
           line 40 (each occurrence
           line 43
           line 54
           line 60
           line 61

UNITED STATES PATENT AND TRADEMARK OFFICE
CERTIFICATE OF CORRECTION

PATENT NO. : 5,219,353
DATED : June 15, 1993
INVENTOR(S) : Thomas Q. Garvey, III; Kathleen Ruddy and Frank V. Gates It is certified that error appears in the above-indentified patent and that said Letters Patent is hereby corrected as shown below:

At each of the following occurrences, change "endoclip" to --clip--:

Column 4, line 14
             line 35
             line 37
             line 55

Column 5, line 9
             line 15
             line 21
             line 22
             lines 22-23
             line 27

Column 6, line 4,
             line 8
             line 11
             line 12,
             line 14
             line 16
             line 18
             line 20
             line 23
             line 27

UNITED STATES PATENT AND TRADEMARK OFFICE
CERTIFICATE OF CORRECTION

PATENT NO.  : 5,219,353
DATED       : June 15, 1993
INVENTOR(S) : Thomas Q. Garvey, III; Kathleen Ruddy and Frank V. Gates It is certified that error appears in the above-indentified patent and that said Letters Patent is hereby corrected as shown below:

```
Column 6, line 4,
         line 8
         line 11
         line 12,
         line 14
         line 16
         line 18
         line 20
         line 23
         line 27
```
In addition column 5, line 20, "are" should read --arm--

Signed and Sealed this

Twenty-fifth Day of October, 1994

Attest:

BRUCE LEHMAN

*Attesting Officer*      *Commissioner of Patents and Trademarks*